United States Patent [19]

Masi et al.

[11] 4,191,756
[45] Mar. 4, 1980

[54] DAUNOMYCIN DERIVATIVES, THEIR AGLYCONES AND THE USE THEREOF

[75] Inventors: Paolo Masi; Antonino Suarato; Luigi Bernardi, all of Milan; Federico Arcamone, Nerviano, all of Italy

[73] Assignee: Farmitalia Carlo Erba S.p.A., Milan, Italy

[21] Appl. No.: 901,359

[22] Filed: May 1, 1978

[30] Foreign Application Priority Data

May 5, 1977 [GB] United Kingdom ............... 18777/77

[51] Int. Cl.² .................. A61K 31/71; C07H 15/24
[52] U.S. Cl. ............................ 424/180; 536/17 R; 536/17 A; 536/18; 260/592
[58] Field of Search ............... 536/17, 17 A; 424/180

[56] References Cited
U.S. PATENT DOCUMENTS

| | | | |
|---|---|---|---|
| 4,025,623 | 5/1977 | Arcamone et al. | 536/17 A |
| 4,039,663 | 8/1977 | Arcamone et al. | 536/17 A |
| 4,067,969 | 1/1978 | Penco et a. | 536/17 A |

Primary Examiner—Johnnie R. Brown
Assistant Examiner—Blondel Hazel
Attorney, Agent, or Firm—Hubbell, Cohen, Stiefel & Gross

[57] ABSTRACT

Daunomycin derivatives of the formula:

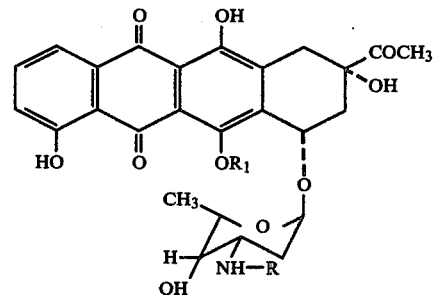

wherein $R_1$ is a lower alkyl having from 1 to 4 carbon atoms and R is a hydrogen atom or a trifluoroacetyl group are useful in treating certain mammalian tumors.

5 Claims, No Drawings

DAUNOMYCIN DERIVATIVES, THEIR AGLYCONES AND THE USE THEREOF

The invention described herein was made in the course of work under a grant from the United States Department of Health, Education and Welfare.

CROSS REFERENCE TO RELATED APPLICATIONS

This application is related to and incorporates by reference the contents of co-pending application Ser. No. 850,933, filed Nov. 14, 1977 and owned by the unrecorded assignee hereof.

BACKGROUND OF THE INVENTION

The invention relates to antitumor compounds which are anthracyclines, and in particular, to a new class of daunomycin derivatives and the aglycones thereof. The invention also relates to the use of these new compounds in treating mammalian tumors. Also within the scope of the invention are certain novel intermediates used in the preparation of the compounds of the invention.

SUMMARY OF THE INVENTION

The invention provides, in one aspect thereof, a new class of daunomycin derivatives of the formula I:

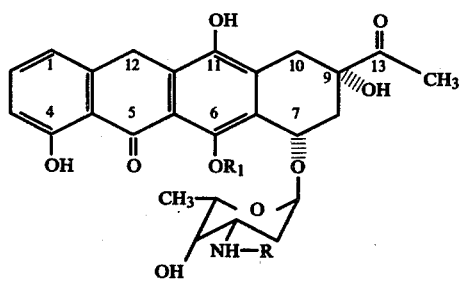

wherein $R_1$ is a lower alkyl having from 1 to 4 carbon atoms and R is hydrogen or a trifluoroacetyl group.

These compounds are prepared from the respective aglycones of the formula II (which are derivatives of daunomycinone) by condensation with an N,O-protected daunosamine derivative. The aglycones of the formula II:

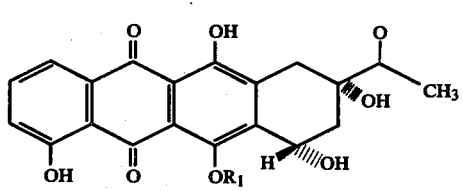

wherein $R_1$ is as defined above, are another aspect of the invention.

The aglycones of the formula II are in turn prepared from daunomycinone III according to the following sequence:

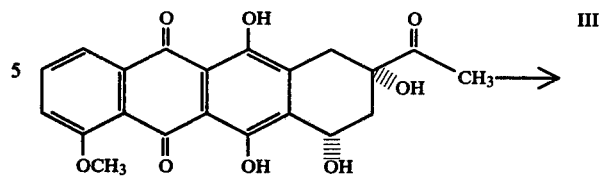

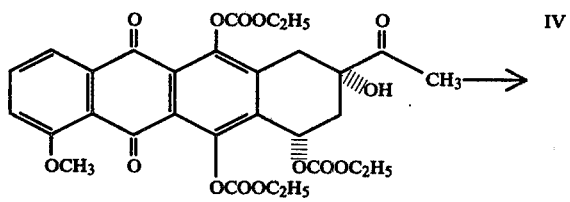

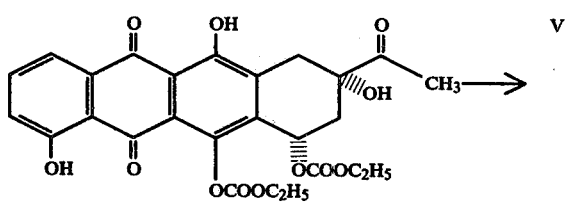

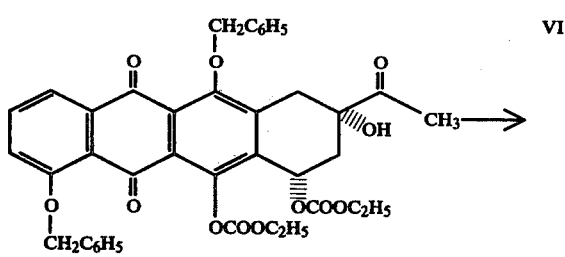

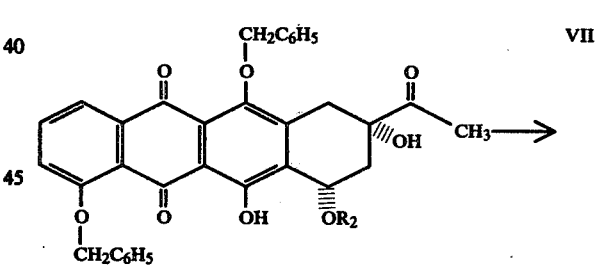

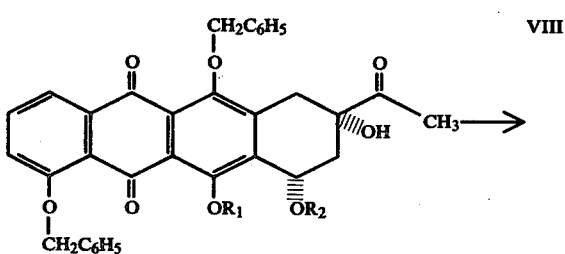

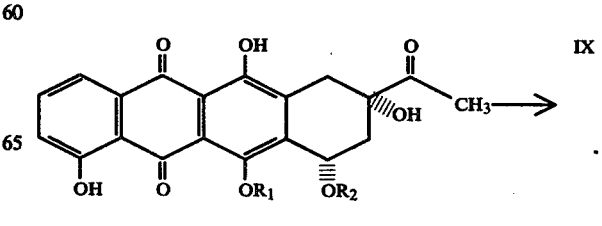

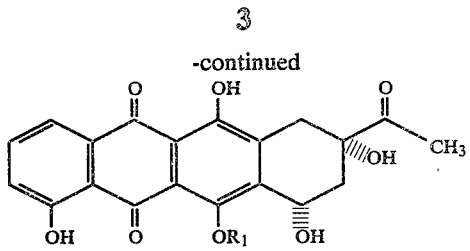

wherein $R_1$ is as defined above and $R_2$ is as defined hereinafter.

As described in co-pending application Ser. No. 850,933, filed Nov. 14, 1977, daunomycinone III can be easily converted to the triethoxycarbonyl derivative IV. We have now surprisingly found that compound IV reacts with aluminum trichloride in an organic solvent such as dichloromethane, chloroform and the like, to afford the bis-phenolic compound V by an unexpected, simultaneous cleavage of the phenolic methyl ether in the 4-position and of the carbonate moiety in the 11-position. Compound V is thus the key intermediate of the present synthesis. In fact, the reaction of compound V with a benzyl halide in the presence of a base such as silver oxide, potassium carbonate and the like, in a suitable organic solvent and at a temperature of 20° to 100° C., yields the dibenzyl derivative VI. The latter, on treatment with a dilute alkaline hydroxide or with an activated basic resin such as AG1-X2 and the like, gives rise to the monophenolic compound VII, wherein $R_2$ is hydrogen when the reaction is carried out in aqueous medium, and preferably, is an alkyl residue when an alcohol, such as methanol, is used as the solvent. Another key step in this synthesis is the reaction of the phenolic hydroxyl group of compound VII ($R_2=CH_3$) with a halide of the general formula $R_1$-Y, wherein $R_1$ is as defined above and Y is Cl, Br, or I, to afford the new ethers of the formula VIII ($R_2=CH_3$). This reaction is run in a boiling organic solvent such as dichloromethane, chloroform, dichloroethane and the like in the presence of a base such as silver oxide, potassium carbonate and the like. Selective removal of the benzylic groups of compound VIII ($R_2=CH_3$) is achieved by brief treatment with trifluoroacetic acid at room temperature with the formation of the bisphenolic compound IX ($R_2=CH_3$). Finally the C-7 methyl ether is hydrolyzed in boiling aqueous trifluoroacetic acid to afford the new aglycone II, together with small amounts of the 7-epimers thereof. The latter can themselves be transformed into aglycones II, having the 7-α-OH, following the equilibration method reported by Kende in J. Am. Chem. Soc. 98, 1967 (1976). The biologically active glycosides of formula I are prepared by condensing an aglycone of the formula II (according to the procedure for the synthesis of glycoside linkages described in Belgian Patent No. 842,930 owned by the unrecorded assignee hereof) with a protected 1-halo-sugar in a suitable organic solvent, such as dichloromethane or chloroform, in the presence of a soluble silver salt as a catalyst. In the present case, the aglycone II is condensed with 1-chloro-N,O-bis-trifluoroacetyl-daunosamine, to form the N,O protected glycoside X wherein $R_1$ is as defined above:

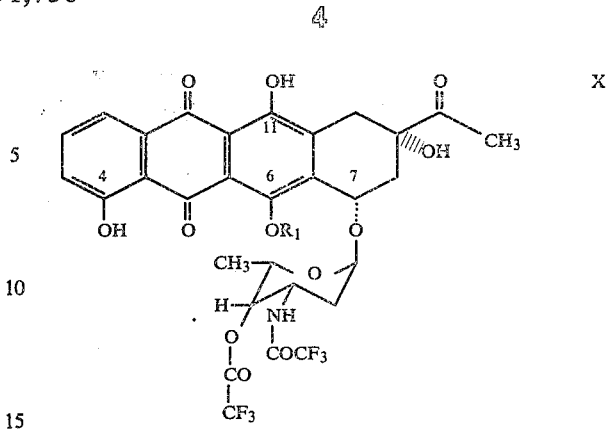

The N,O protected glycoside X, on treatment with methanol and a catalytic amount of triethylamine, is converted into the N-trifluoroacetyl protected glycoside which can be successively hydrolyzed, by mild exposure to a dilute alkaline base, to form the free glycosidic base which is finally isolated as the hydrochloride. Compounds I display antimitotic activity and they are useful therapeutic agents for the treatment of certain mammalian tumors.

DESCRIPTION OF THE PREFERRED EMBODIMENTS

The following examples are given to illustrate the invention by describing the preparation of compounds according to the invention and their use, without, however, being a limitation thereof.

EXAMPLE 1

4-Demethoxy-4-hydroxy-$O^6,O^7$-bis-ethoxycarbonyl-daunomycinone

To a solution of 30 g. of $O^6,O^7,O^{11}$-tris-ethoxycarbonyldaunomycinone in 500 ml. of chloroform, 30 g. of granular aluminum trichloride were added under vigorous stirring. Two further additions, each one of 30 g. of aluminum trichloride, were made after 1 hour and 1.5 hours, respectively. After stirring for two hours, the reaction mixture was poured into 2 liters of a cold aqueous solution of oxalic acid and extracted with chloroform. The organic layer (chloroform) was washed with an aqueous solution of sodium bicarbonate, then with water and finally was dried over sodium sulfate. The solvent was evaporated in vacuo and the residue was crystallized from a mixture of ethyl acetate-benzene to yield 13 g. of 4-demethoxy-4-hydroxy-$O^6,O^7$-bis-ethoxycarbonyldaunomycinone.

PMR (CDCl$_3$): 1.33 and 1.43 δ (two t, CH$_3$-C(H$_2$)), 2.40 δ (s, CH$_3$CO), 4.23 and 4.33 δ (two q, CH$_2$-C(H$_3$)), 6.13 δ (broad s, C-7-H), 6.9-7.8 δ (m, 3 aromatic protons), 12.45 and 13.4 δ (two s, phenolic hydroxyls).

IR (KBr): 1775, 1750, 1710, 1625, 1600 and 1585 cm$^{-1}$

EXAMPLE 2

4-Demethoxy-4-hydroxy-11-deoxy-4,11-dibenzyloxy-$O^6,O^7$-bis-ethoxycarbonyldaunomycinone A solution of 5 g. of 4-demethoxy-4-hydroxy-$O^6,O^7$-bis-ethoxycarbonyldaunomycinone in 250 ml. of dichloromethane was treated with 5 ml. of benzyl bromide and 5 g. of silver oxide and refluxed for two hours. After cooling, the reaction mixture was filtered and the solvent evaporated in vacuo. The resulting oily residue was washed several times with petroleum ether until it became solid and was then crystallized from a mixture of dichloromethane-benzene to afford 6 g. of 4-demethoxy-4-hydroxy-11-deoxy-4,11-dibenzyloxy-$O^6,O^7$-bis-ethoxycarbonyldaunomycinone.

PMR (CDCl$_3$): 1.30 and 1.40 δ (two t, CH$_3$-C(H$_2$)), 2.23 δ (s, CH$_3$CO), 4.23 and 4.30 δ (two q, CH$_2$-C(H$_3$)), 5.00 and 5.23 δ (two s, O-CH$_2$-C$_6$(H$_5$)), 6.23 δ (broad s, C-7-H), 6.9-7.9 δ (m, 3 aromatic protons).

IR (KBr): 1770, 1745, 1717, 1680 and 1590 cm$^{-1}$.

EXAMPLE 3

4-Demethoxy-4-hydroxy-7,11-bis-deoxy-4,11-dibenzyloxy-7-methoxydaunomycinone A solution of 5 g. of 4-demethoxy-4-hydroxy-11-deoxy-4,11-dibenzyloxy-$O^6,O^7$-bis-ethoxycarbonyldaunomycinone in 15 ml. of dichloromethane and 100 ml. of methanol was treated with an excess of AG1-X2 resin which had been previously activated with aqueous sodium hydroxide and washed with methanol. The reaction mixture was stirred at room temperature until the starting material had completely reacted, and then it was filtered and evaporated to dryness. The resulting residue was chromatographed (silica gel; chloroform-acetone 95:5, v/v) to give 3 g. of 4-demethoxy-4-hydroxy-7,11-bis-deoxy-4,11-dibenzyloxy-7-methoxydaunomycinone.

PMR (CDCl$_3$): 2.30 δ (s, CH$_3$CO), 3.60 δ (s, CH$_3$O), 4.93 δ (s, O-CH$_2$-C$_6$(H$_5$) and C-7-H), 5.31 δ (s, O-CH$_2$-C$_6$(H$_5$)), 7.2-8.0 δ (m, 3 aromatic protons), 14.2 δ (s, phenolic hydroxyl).

IR (KBr): 1726, 1681, 1629, 1587 and 1572 cm$^{-1}$.

EXAMPLE 4

4-Demethoxy-4-hydroxy-11-deoxy-4,11-dibenzyloxydaunomycinone

The title compound was obtained from 4-demethoxy-4-hydroxy-11-deoxy-4,11-dibenzyloxy-$O^6,O^7$-bis-ethoxycarbonyldaunomycinone following the procedure described in Example 3, except that aqueous dichloromethane and wet resin were used in place of the methanol.

PMR (CDCl$_3$): 2.26 δ (s, CH$_3$CO), 4.90 δ (s, O-CH$_2$-C$_6$(H$_5$)), 5.30 δ (s, O-CH$_2$C$_6$(H$_5$) and C-7-H), 6.9-7.9 δ (m, 3 aromatic protons), 14.3 δ (phenolic OH).

EXAMPLE 5

4-Demethoxy-4-hydroxy-6,7,11-tris-deoxy-4,11-dibenzyloxy-6,7-dimethoxydaunomycinone 1.5 Grams of 4-demethoxy-4-hydroxy-7,11-bis-deoxy-4,11-dibenzyloxy-7-methoxy-daunomycinone were dissolved in 200 ml. of dichloromethane containing 20 ml. of methyl iodide and refluxed under stirring in the presence of 1.5 g. of silver oxide. After 24 hours the reaction mixture was cooled and left to stand overnight at room temperature. The inorganic solid which precipitated was filtered off and the solvent evaporated in vacuo to yield 4-demethoxy-4-hydroxy-6,7,11-tris-deoxy-4,11-dibenzyloxy-6,7-dimethoxydaunomycinone in almost quantitative yield.

PMR (CDCl$_3$): 2.33 δ (s, CH$_3$CO), 3.53 and 3.93 δ (two s, CH$_3$O), 5.00 and 5.26 δ (two s, O-CH$_2$-C$_6$(H$_5$)), 7.0-7.9 δ (m, 3 aromatic protons).

EXAMPLE 6

4-Demethoxy-4-hydroxy-6,7-bis-deoxy-6,7-dimethoxydaunomycinone 1.5 Grams of 4-demethoxy-4-hydroxy-6,7,11-tris-deoxy-4,11-dibenzyloxy-6,7-dimethoxydaunomycinone were dissolved in 50 ml. of trifluoroacetic acid containing 2% of water and the solution was left to stand at room temperature for 3 hours. The acid was removed in vacuo and the residue dissolved in the minimum amount of acetone, treated with concentrated aqueous ammonia and finally diluted with ethyl acetate. After several washings with water, the organic layer was dried over anhydrous sodium sulfate. The solvent was removed in vacuo to afford 4-demethoxy-4-hydroxy-6,7-bis-deoxy-6,7-bis-methoxydaunomycinone in 90% yield.

PMR (CDCl$_3$): 2.40 δ (s, CH$_3$CO), 3.56 and 3.90 δ (two s, CH$_3$O), 4.80 δ (broad s, C-7-H), 6.7-7.8 δ (m, 3 aromatic protons), 12.9 and 13.5 δ (aromatic hydroxyls).

EXAMPLE 7

4-Demethoxy-4-hydroxy-6-deoxy-6-methoxydaunomycinone and its 7-epimer

A solution of 1.5 g. of 4-demethoxy-4-hydroxy-6,7-bis-deoxy-6,7-bis-methoxydaunomycinone in 50 ml. of trifluoroacetic acid containing 2% of water was kept at 60° C. for 2 hours. The acid was removed in vacuo and the residue dissolved in acetone and hydrolyzed with concentrated aqueous ammonia. The reaction mixture was diluted with chloroform, washed with water and evaporated to dryness. The resulting residue was chromatographed (silica gel; chloroform-acetone 95:5, v/v) to give two products: 4-demethoxy-4-hydroxy-6-deoxy-6-methoxydaunomycinone (Rf 0.43 on silica gel plate; chloroform-acetone 4:1, v/v) and its 7-epimer (Rf 0.3) in a ratio of 8:2. If desired, the 7-epimer can be readily converted to the natural configuration by treatment with trifluoroacetic acid.

PMR (CDCl$_3$) of 4-demethoxy-4-hydroxy-6-deoxy-6-methoxydaunomycinone: 2.43 δ (s, CH$_3$CO), 3.96 δ (s, CH$_3$O), 5.20 δ (broad s, C-7-H), 7.0-7.8 δ (m, 3 aromatic protons), 12.8 and 13.5 δ (two s, phenolic hydroxyls).

IR (CDCl$_3$): 1718, 1625 and 1585 cm$^{-1}$.

EXAMPLE 8

4-Demethoxy-4-hydroxy-6-deoxy-6-methoxy-N-trifluoroacetyldaunomycin

To a solution of 1.5 g. of 4-demethoxy-4-hydroxy-6-deoxy-6-methoxydaunomycinone and 1.25 g. of 2,3,6-trideoxy-3-trifluoroacetamido-4-O-trifluoroacetyl-α-L-lyxopyranosyl chloride (1-chloro-N,O-bis-trifluoroacetyldaunosamine) in 100 ml. of anhydrous dichloromethane, a solution of 0.95 g. of silver trifluoromethanesulphonate in anhydrous diethyl ether was added dropwise at room temperature under stirring. After 1 hour, the reaction mixture was washed with aqueous NaHCO$_3$ and evaporated to dryness. The resulting residue was dissolved in methanol containing a catalytic amount of triethylamine and left to stand at room temperature for 2 hours. The solvent was removed in vacuo and the residue chromatographed (silica gel; chloroform-acetone 95:5, v/v) to give pure 4-demethoxy-4-hydroxy-6-deoxy-6-methoxy-N-trifluoroacetyldaunomycin.

PMR (CDCl$_3$): 1.31 δ (d, CH$_3$-C(H)<), 2.40 δ (s, CH$_3$-CO), 3.86 δ (s, CH$_3$O), 5.20 (s, C-7-H), 5.36 δ (s,

C-1'-H) 7.0–7.9 δ (m, aromatic H), 12.83 and 13.53 δ (two s, phenolic H).

EXAMPLE 9

4-Demethoxy-4-hydroxy-6-deoxy-6-methoxydaunomycin hydrochloride 1.0 Gram of 4-demethoxy-4-hydroxy-6-deoxy-6-methoxy-N-trifluoroacetyldaunomycin was dissolved in 50 ml. of aqueous 0.15 N NaOH and left to stand for 1 hour at room temperature. After acidification with oxalic acid and rapid neutralization with aqueous NaHCO₃, the product was extracted with chloroform and the chloroform extract was evaporated to dryness. The resulting residue was dissolved in dichloromethane and treated with 1 equivalent of HCl in methanol. Upon the addition of diethyl ether, 4-demethoxy-4-hydroxy-6-deoxy-6-methoxydaunomycin hydrochloride was precipitated and collected by filtration.

Rf=0.58 (CHCl₃-CH₃OH-H₂O=13:6:1 v/v)
λmax=481 nm.
PMR (CDCl₃): 1.26 δ (d, CH₃-C(H)<), 2.40 δ (s, CH₃CO), 3.90 δ (s, CH₃O), 5.20 δ (s, C-7-H), 5.36 δ (s, C-1'-H), 7.0–7.9 δ (m, aromatic H).

BIOLOGICAL ACTIVITY

4-Demethoxy-4-hydroxy-6-deoxy-6-methoxydaunomycin was tested under the auspices of N.C.I., National Institute of Health, Bethesda, Maryland, U.S.A. against Lymphocytic Leukemia P₃₈₈ according to the procedure described in Cancer Chemotherapy Reports, Part 3, Vol. 3, page 9 (1972). The following Table illustrates the antitumor activity of this new anthracycline compound.

The new compound was compared to daunomycin in a test in which mice infected with tumor cells were injected with the two compounds on days 5, 9 and 13 with a 4 day interval between each single injection starting from the fifth day after tumor transplantation in mice.

TABLE

| Compound | Schedule of Treatment in Days (i.p.) | Dose mg./kg. | T/C % |
|---|---|---|---|
| Daunomycin . HCl | 5,9,13 | 32.0 | 109 |
| 4-Demethoxy-4-hydroxy-6-deoxy-6-methoxy-daunomycin . HCl | 5,9,13 | 16.0 | 148 |
| | | 8.0 | 129 |
| | | 4.0 | 120 |
| | | 2.0 | 119 |
| | | 50.0 | 124 |
| | | 25.0 | 129 |
| | | 12.5 | 129 |
| | | 6.25 | 118 |
| | | 3.13 | 114 |

Modifications and variations can, of course, be made without departing from the spirit and scope of the invention.

Having thus described our invention, what we desire to secure by Letters Patent and hereby claim is:

1. A compound of the formula I:

wherein R₁ is a lower alkyl having from 1 to 4 carbon atoms and R is a hydrogen atom or a trifluoroacetyl group, and the hydrochlorides thereof.

2. A compound according to claim 1, which is 4-demethoxy-4-hydroxy-6-deoxy-6-methoxy-N-trifluoroacetyldaunomycin.

3. A compound according to claim 1, which is 4-demethoxy-4-hydroxy-6-deoxy-6-methoxydaunomycin hydrochloride.

4. A pharmaceutical composition comprising a therapeutically effective amount of a compound according to claim 1, in combination with a carrier therefor.

5. A method of treating a host afflicted with transplanted leukemia P₃₈₈ which comprises intraperitoneally administering to said host a compound according to claim 1 in an amount sufficient to inhibit the growth thereof.

* * * * *

UNITED STATES PATENT OFFICE
CERTIFICATE OF CORRECTION

Patent No. 4,191,756   Dated March 4, 1980

Inventor(s) Paolo Masi et al

It is certified that error appears in the above-identified patent and that said Letters Patent are hereby corrected as shown below:

Column 1, lines 34-44:

" 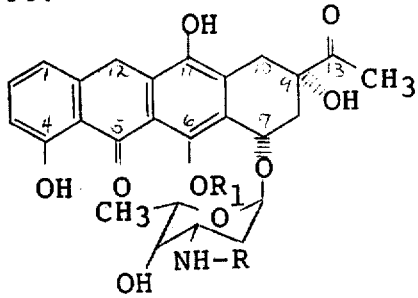 " should read:

-- 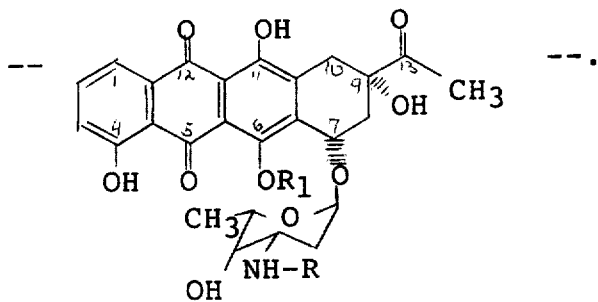 --.

Column 1, lines 55-62:

" 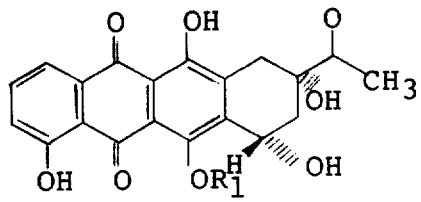 "

UNITED STATES PATENT OFFICE
CERTIFICATE OF CORRECTION

Patent No. 4,191,756   Dated March 4, 1980

Inventor(s) Paolo Masi et al

It is certified that error appears in the above-identified patent and that said Letters Patent are hereby corrected as shown below:

should read: -- 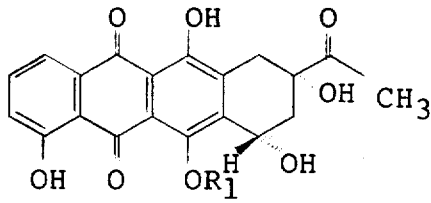 --.

Signed and Sealed this

Thirtieth Day of September 1980

[SEAL]

Attest:

SIDNEY A. DIAMOND

Attesting Officer    Commissioner of Patents and Trademarks